(12) United States Patent
Bassler et al.

(10) Patent No.: US 7,658,893 B2
(45) Date of Patent: Feb. 9, 2010

(54) METHOD FOR THE CONTINUOUS PRODUCTION OF PROPYLENE GLYCOL

(75) Inventors: Peter Bassler, Viernheim (DE); Hans-Georg Goebbel, Kallstadt (DE); Joaquim Henrique Teles, Otterstadt (DE); Peter Rudolf, Ladenburg (DE)

(73) Assignee: BASF Aktiengesellschaft, Ludwigshafen (DE)

(*) Notice: Subject to any disclaimer, the term of this patent is extended or adjusted under 35 U.S.C. 154(b) by 413 days.

(21) Appl. No.: 11/441,153

(22) Filed: May 26, 2006

(65) Prior Publication Data

US 2006/0216216 A1 Sep. 28, 2006

Related U.S. Application Data

(62) Division of application No. 10/521,467, filed on Jan. 18, 2005, now Pat. No. 7,084,310.

(51) Int. Cl.
*B01J 19/00* (2006.01)
*C07C 29/80* (2006.01)
*C07C 29/09* (2006.01)

(52) U.S. Cl. .................. 422/189; 422/187; 568/868; 568/867

(58) Field of Classification Search ............... None
See application file for complete search history.

(56) References Cited

U.S. PATENT DOCUMENTS 2,471,134 A 5/1949 Wright
4,230,533 A 10/1980 Giroux
4,937,393 A 6/1990 Masuda et al.
6,479,680 B1 * 11/2002 Bassler et al. ............... 549/529

FOREIGN PATENT DOCUMENTS

| DE | 100 22 465 | 11/2001 |
| DE | 101 05 527 | 8/2002 |
| EP | 0 031 537 | 7/1981 |
| EP | 0 122 367 | 10/1984 |
| EP | 0 126 288 | 11/1984 |
| EP | 0 133 510 | 2/1985 |
| EP | 0 780 147 | 6/1997 |
| GB | 2 068 408 | 8/1981 |
| WO | 99/31034 | 6/1999 |
| WO | 00/07965 | 2/2000 |

OTHER PUBLICATIONS

Elm, Rainer et al. "Propandiole", Ullmann's Encyclopaedie der Technischen Chemie, 4th edition, vol. 19, pp. 425-432.
Kaibel, Gerd. "Distillation Columns with Vertical Partitions", Chem. Eng. Technol., vol. 10, pp. 92-98 1987.
Kaibel, Gerd et al. "Gestaltung destillativer Trennungen unter Einbeziehung thermodynamischer Gesichtspunkte", Chem.-Ing. Tech., vol. 61, No. 1, pp. 16-25, with English abstract 1989.

(Continued)

*Primary Examiner*—Jennifer A Leung
(74) *Attorney, Agent, or Firm*—Oblon, Spivak, McClelland, Maier & Neustadt, L.L.P.

(57) ABSTRACT

An apparatus for carrying out a continuous process for preparing propylene glycols.

14 Claims, 1 Drawing Sheet

OTHER PUBLICATIONS

Kaibel, G. et al. "Thermodynamics- guideline for the development of distillation column arrangements", Gas Separation & Purification, vol. 4, pp. 109-114 1990.
"Designs on Mixing", Process Engineering, vol. 2, pp. 33-34 1993.
Lestak, F. et al. "Heat Transfer Across the Wall of Dividing Wall Columns", Trans IChemE, vol. 72, Part A, pp. 639-644 1994.

Lestak, Frigyes et al. "Advanced Distillation Saves Energy & Capital", Chemical Engineering, vol. 7, pp. 72-76 1997.

"Hydrogen Peroxide", Ullmann's Encyclopedia of Industrial Chemistry 5$^{th}$ edition, vol. A13, pp. 447-456.

* cited by examiner

Figure

METHOD FOR THE CONTINUOUS PRODUCTION OF PROPYLENE GLYCOL

CROSS REFERENCE TO RELATED APPLICATIONS

This application is a divisional application of U.S. patent application Ser. No. 10/521,467 filed on Jan. 18, 2005 that issued as U.S. Pat. No. 7,084,310 on Aug. 1, 2006.

FIELD OF THE INVENTION

The present invention relates to a process for the continuous preparation of propylene glycols by reaction of propylene with hydrogen peroxide to give propylene oxide with simultaneous or subsequent glycol formation and joint work-up. The glycols are separated from the product mixture by distillation, with propylene glycol and dipropylene glycol being separated off in a dividing wall column having two side offtakes and tripropylene glycol being separated off in a column which is thermally coupled with the dividing wall column. The invention also relates to an apparatus for carrying out the process.

BACKGROUND OF THE INVENTION

Propylene glycol and polypropylene glycols are important intermediates, for example, for producing polyester and epoxy resins and also polyurethane forms. Their industrial preparation has hitherto mostly been carried out using a 3-stage process.

In this process, propylene oxide is reacted with a stoichiometric excess of water at from 180 to 220° C. and a pressure of from 15 to 25 bar in a first stage. Tube reactors connected in series are generally used for this reaction. The propylene glycols obtained are then present in the form of a mixture comprising propylene glycol, also known as monopropylene glycol or 1,2-propylene glycol, dipropylene glycol and tripropylene glycol in a weight ratio of about 100:10:1. This mixture is transferred, in a second stage, to a dewatering apparatus in which the excess water is separated off in a multistage evaporation and is returned to the reaction. Finally, in a third stage, the propylene glycols are distilled to give pure products. According to the prior art, this is carried out using three columns which are connected in series and each have a side offtake. In the first column, the propylene glycol is obtained from the side offtake and the bottoms are passed to the second column from whose side offtake the dipropylene glycol is obtained. The mixture from the bottom of this second column is passed to the third column from whose side offtake the tripropylene glycol can finally be obtained (Ullmann's Encyclopadie der technischen Chemie, 4th Edition, Volume 19, pages 425-432).

The process described requires a high outlay in terms of apparatus and energy, particularly in the process step in which the three propylene glycols mentioned are separated by distillation, since three columns are used. Furthermore, it requires the use of pure propylene oxide as starting material.

DETAILED DESCRIPTION OF THE INVENTION

It is an object of the present invention to provide an improved process for preparing the propylene glycols. In particular, the process of the present invention should make it possible to use propylene oxide of low purity as starting material and allow the separation of the propylene glycols mentioned to be carried out with a reduced outlay in terms of apparatus and energy.

We have found that this object is achieved by a process in which the preparation of propylene oxide in which some propylene glycols are formed as by-products is coupled with the reaction of the propylene oxide with water. The propylene oxide is preferably prepared by reaction of propylene with peroxides, for example, hydrogen peroxide. The propylene glycols are separated off by distillation in a dividing wall column having two liquid side offtakes and a column which is thermally coupled therewith.

The present invention accordingly provides a process for the continuous preparation of propylene glycols, which comprises at least the steps (i) to (iii):

(i) reacting propylene with hydrogen peroxide to form propylene oxide and propylene glycols,
(ii) reacting the propylene oxide obtained in step (i) with water to give propylene glycols,
(iii) separating off the propylene glycols obtained in steps (i) and (ii).

In a preferred embodiment, the separation in step (iii) is carried out by distillation in a dividing wall column having two side offtakes and a column which is thermally coupled therewith, with propylene glycol being obtained from the upper side offtake of the dividing wall column, dipropylene glycol being obtained from the lower side offtake and tripropylene glycol being obtained from the column which is thermally coupled therewith.

In the novel process, it is thus no longer necessary to use pure propylene oxide in the reaction with water, but instead it is possible to use the crude product, which already contains amounts of the propylene glycols, obtained in the synthesis of propylene oxide from propylene and hydrogen peroxide. The use of the dividing wall column in combination with the thermally coupled column can, in addition, enable considerable savings to be achieved in terms of apparatus and energy consumption compared to the prior art, since only two columns instead of three are necessary for separating off the glycols. The continuous process thus offers advantages compared to the process of the prior art.

The preparation of propylene oxide by reaction of propylene with hydrogen peroxide in step (i) is known and can be carried out by known methods. Both single-stage and multistage processes can be used. Owing to their economic advantages multistage processes are preferred.

For example, the multistage process described in WO 00/07965 provides for the reaction of propylene with hydrogen peroxide to form propylene oxide to comprise at least the steps ($\alpha$) to ($\gamma$):

($\alpha$) reacting propylene with hydrogen peroxide to give a mixture comprising propylene oxide and unreacted hydrogen peroxide,
($\beta$) separating the unreacted hydrogen peroxide from the mixture resulting from step ($\alpha$),
($\gamma$) reacting the hydrogen peroxide which has been separated off in stage ($\beta$) with propylene.

Accordingly, in this reaction sequence, the reaction of propylene with hydrogen peroxide takes place in at least two steps ($\alpha$) and ($\gamma$), with the hydrogen peroxide separated off in step ($\beta$) being used in the reaction again.

In this sequence, said reaction is preferably carried out over a heterogeneous catalyst, optionally using a solvent such as methanol.

The reactions in steps ($\alpha$) and ($\gamma$) preferably take place in two separate reactors. Fixed-bed reactors are usually employed for this purpose, with the reaction of step ($\alpha$) being carried out in an isothermal reactor and the reaction of step ($\gamma$) being carried out in an adiabatic reactor.

The hydrogen peroxide conversion in step (α) is generally from about 85% to 90% and that in step (γ) it is about 95% based on step (β). Overall, a hydrogen peroxide conversion of about 99% over both stages can be achieved at a propylene oxide selectivity of about 94-95%.

The mixture obtained in the reaction generally contains from about 6 to 10% by weight of propylene oxide. Further components present are, for example, methanol as solvent, water, unreacted propylene as organic compound and hydrogen peroxide and also acetaldehyde and methyl formate.

The water present in the product mixture originates from the reaction of the hydrogen peroxide with propylene and also decomposition of the hydrogen peroxide. Furthermore, an aqueous hydrogen peroxide solution is preferably used in steps (α) and (γ). Under the prevailing conditions, water may react with propylene oxide to form propylene glycol. The glycol formed in this way as by-product can in turn react further with additional propylene oxide to give dipropylene glycol and tripropylene glycol. Thus, monopropylene glycol, dipropylene glycol and tripropylene glycol are present in addition to the propylene oxide. These glycols can readily be separated by distillation from the product mixture containing the propylene oxide since they have relatively high boiling points. When the distillation is carried out in a column, they are obtained in the bottoms while propylene oxide together with further volatile components is distilled off via the top of the column. This propylene oxide has a purity of from about 95 to 99% and is referred to as crude propylene oxide.

The 1- and 2-methoxypropanols obtained as further by-products by subsequent reaction of propylene oxide with methanol under the reaction conditions are also obtained in the bottoms. Further by-products present in the bottoms are 2-hydroperoxy-1-propanol and 1-hydroperoxy-2-propanol which are formed by addition of hydrogen peroxide on to propylene oxide.

These hydroperoxy alcohols are preferably reduced, likewise forming propylene glycol. For example, the methods described in DE 101 05 527.7 can be used for the reduction. A preferred reduction method is catalytic hydrogenation.

In one embodiment of the process of the present invention, the propylene glycol obtained as by-product in step (i) is accordingly formed by reduction of 2-hydroperoxy-1-propanol and 1-hydroperoxy-2-proanol.

There is therefore a second possible way of propylene glycol being formed as by product in addition to the reaction of propylene oxide with water.

For the purposes of further reaction, it is extremely advantageous for the crude propylene oxide to be able to be used in the process of the present invention without further purification.

The crude propylene oxide is then reacted with water to give a mixture of propylene glycols. The reaction can advantageously be carried out using the process described in the prior art and the reaction conditions and reactors indicated therein. However, all possible processes for the catalytic addition of water on to propylene oxide can also be employed, for example, the method described in WO 99/31034.

The crude propylene oxide is preferably reacted with a stoichiometric excess of water at from 180 to 220° C. and a pressure in the range from 15 to 25 bar, for instance in a tube reactor or tube reactors connected in series. The propylene glycols formed are then present in the form of a mixture consisting essentially of propylene glycol, dipropylene glycol, tripropylene glycol and polypropylene glycols.

In one embodiment of the process of the present invention, propylene oxide is therefore reacted with water at from 180 to 220° C. and a pressure of from 15 to 25 bar in step (ii).

The residence times in the reactor or reactors depend essentially on the desired conversions. They are generally less than 5 hours, preferably less than 3 hours, more preferably less than 1 hour and particularly preferably about half an hour.

The mixture obtained in step (ii) is preferably transferred to a dewatering apparatus in which the excess water is separated off in a multistage evaporation. This water can be returned to the reaction with the propylene oxide. As apparatuses for dewatering, it is possible to use conventional distillation columns in which the water is distilled off via the top as a low-boiling fraction. The glycol mixture can be isolated at the bottom or via the side offtake of such apparatuses.

In a preferred embodiment of the process of the present invention, the water is accordingly removed from the mixture obtained in step (ii) before the propylene glycols are separated off in step (iii).

The mixture obtained in the dewatering step preferably has a residual water content of less than 5% by weight before it is transferred to the apparatus in which the propylene glycols are to be separated off.

The glycols obtained in step (i) and step (ii) are then separated off in step (iii). Here, the glycol mixture which has been obtained and separated off as secondary yield in step (i), as described above, is combined with the glycol mixture obtained from the dewatering step and the two are distilled together to separate off the individual glycols.

Before the glycol mixtures from step (i) and step (ii) are combined, the methoxypropanols and the solvent, namely, methanol, present in the mixture from step (i) are preferably separated off.

According to the present invention, a feed stream comprising the glycol mixture is then fed continuously into a dividing wall column. According to the present invention, use is made of a dividing wall column having two side offtakes which are located one above the other and a column which is thermally coupled therewith and into which a stream from the lower region of the dividing wall column is fed. The thermally coupled column is a conventional rectification column which is operated without a vaporizer. The heat required for operation of this column is introduced via the vapor stream.

Dividing wall columns are known from the prior art. They represent a further development of distillation columns which have only a side offtake but no dividing wall. The use of the last-named conventional type of column is, however, restricted because the products taken off at the side offtakes are never completely pure. In the case of products taken off at side offtakes in the enrichment section of the column, which are usually taken off in liquid form, the side product still contains proportions of low-boiling components which should be separated off via the top. In the case of products taken off at side offtakes in the stripping section of the column, which are usually taken off in gaseous form, the side product still contains proportions of high boilers. The use of conventional side offtake columns is therefore restricted to cases in which contaminated side products are permissible.

When a dividing wall is installed in such a column, the separation action can be improved and it becomes possible for side products to be taken off in pure form. A dividing wall is installed in the middle region above and below the feed point and the side offtakes. This can be fixed in place by welding or can be merely pushed into place. It seals off the offtake part from the inflow part and prevents crossmixing of liquid and vapor streams over the entire column cross section in this part of the column. This reduces the total number of distillation columns required in the fractionation of multicomponent mixtures whose components have similar boiling points.

This type of column has been used, for example, for the separation of an initial mixture of the components methane, ethane, propane and butane (U.S. Pat. No. 2,471,134), for the separation of a mixture of benzene, toluene and xylene (U.S. Pat. No. 4,230,533), for the separation of a mixture of n-hexane, n-heptane and n-octane (EP 0 122 367), for the separation of azeotropically boiling mixtures (EP 0 133 510) and for carrying out chemical reactions with simultaneous distillation of the products (EP 0 126 288).

Figure 1:
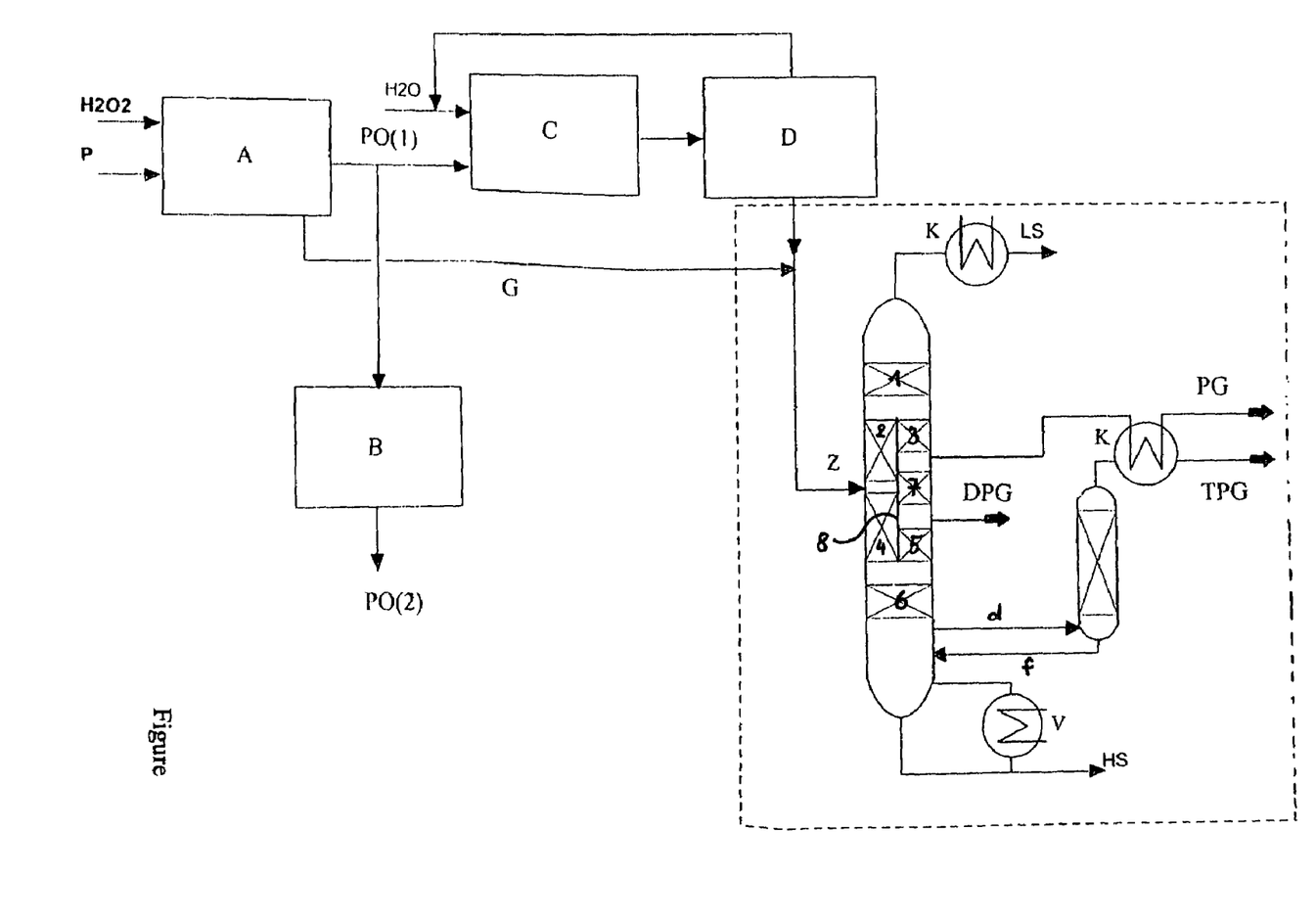
The FIGURE depicts an inventive apparatus embodiment.

Such a dividing wall column, as shown schematically in the figure, preferably has from 15 to 60, more preferably from 20 to 40, theoretical plates. The process of the invention can be carried out particularly advantageously using such a design.

The upper combined region 1 of the inflow and offtake part of the column preferably has from 5 to 50%, more preferably from 15 to 30%, the enrichment section 2 of the inflow part preferably has from 5 to 50%, more preferably from 15 to 30%, the stripping section 4 of the inflow part preferably has from 5 to 50%, more preferably from 15 to 30%, the stripping section 3 of the offtake part preferably has from 5 to 50%, more preferably from 15 to 30%, the enrichment section 5 of the offtake part preferably has from 5 to 50%, more preferably from 15 to 30%, the lower combined region 6 of the inflow and offtake part of the column preferably has from 5 to 50%, more preferably from 15 to 30%, and the region of thermal coupling 7 of the two side offtakes preferably has from 5 to 50%, more preferably from 15 to 30%, in each case of the total number of theoretical plates in the column.

The sum of the number of theoretical plates in the regions 2 and 4 in the inflow part is preferably from 80 to 110%, more preferably from 90 to 100%, of the sum of the number of theoretical plates in the regions 3, 5 and 7 in the offtake part.

It is likewise advantageous for the feed point Z and the side offtakes from which the glycols PG and DPG are taken to be arranged at different heights in the column relative to the position of the theoretical plates. The feed point Z is preferably located at a position which is from 1 to 8, more preferably from 3 to 5, theoretical plates above or below the side offtakes.

The dividing wall column used in the process of the present invention is preferably configured as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical plate.

In the abovementioned configuration of the column, the region of the column divided by the dividing wall 8, which consists of the enrichment section 2 of the inflow part, the stripping section 3 of the offtake part, the stripping section 4 of the inflow part and the enrichment section 5 of the offtake part or parts thereof is/are provided with ordered packing or random packing. The dividing wall can be thermally insulated in these regions.

The product stream is advantageously metered by means of a pump or via a static inflow head of at least 1 m into the inflow part. This inflow is preferably regulated via a cascade regulation in combination with the regulation of the liquid level in the inflow part. The regulation is set so that the amount of liquid introduced into the enrichment section cannot drop below 30% of the normal value. It has been found that such a procedure is important to even out troublesome fluctuations in the amount or concentration of the feed.

It is likewise important for the division of the liquid flowing down from the stripping section of the offtake part of the column between the side offtake and the enrichment section of the offtake part to be set by means of a regulation device so that the amount of liquid going to the enrichment section cannot drop below 30% of the normal value.

Adherence to these prerequisites has to be ensured by means of appropriate regulation methods.

Regulation mechanisms for the operation of dividing wall columns have been described, for example, in Chem. Eng. Technol. 10 (1987) 92-98, Chem.-Ing.-Technol. 61 (1989) No. 1, 16-25, Gas Separation and Purification 4 (1990) 109-114, Process Engineering 2 (1993) 33-34, Trans IChemE 72 (1994) Part A 639-644, Chemical Engineering 7 (1997) 72-76). The regulation mechanisms described in this prior art can also be employed for or applied to the process of the present invention.

The regulation principle described below has been found to be particularly useful for the continuously operated isolation of the glycols. It is readily able to cope with fluctuations in loading. The distillate is thus preferably taken off under temperature control.

A temperature regulation device which utilizes the downflow quantity, the reflux ratio or preferably the quantity of runback as regulating parameter is provided in the upper section 1 of the column. The measurement point for the temperature regulation is preferably located from 3 to 8, more preferably from 4 to 6, theoretical plates below the upper end of the column.

Appropriate setting of the temperature then results in the liquid flowing down from the upper section 1 of the column being divided at the upper end of the dividing wall 8 so that the ratio of the liquid flowing to the inflow part to that flowing to the offtake part is preferably from 0.1 to 1.0, more preferably from 0.3 to 0.6.

In this method, the down flowing liquid is preferably collected in a receiver which is located in or outside the column and from which the liquid is then fed continuously into the column. This receiver can thus take on the task of a pump reservoir or provide a sufficiently high static head of liquid which makes it possible for the liquid to be passed on further in a regulated manner by means of regulating devices, for example, valves. When packed columns are used, the liquid is firstly collected in collectors and from there conveyed to an internal or external receiver.

The vapor stream at the lower end of the dividing wall 8 is set by selection and/or dimensioning of the separation internals and/or installation of pressure-reducing devices, for example, orifice plates, so that the ratio of the vapor stream in the inflow part to that in the offtake part is preferably from 0.8 to 1.2, preferably from 0.9 to 1.1.

In the abovementioned regulation principle, a temperature regulation device which utilizes the quantity taken off at the bottom as regulating parameter is provided in the lower combined section 6 of the column. The bottom product can thus be taken off under temperature control. The measurement point for the temperature regulation device is preferably located from 3 to 6, more preferably from 4 to 6, theoretical plates above the lower end of the column.

In addition, the level regulation in the bottom of the column can be provided as regulating parameter for the abovementioned regulation of the quantity taken off at the lower side offtake and a temperature regulation in the divided column region can be provided for the quantity taken off at the upper side offtake.

The differential pressure over the column can also be used as regulating parameter for the heating power. The distillation is advantageously carried out at a pressure at the top of from 5 to 500 mbar, preferably from 10 to 200 mbar. Accordingly, the heating power of the vaporizer at the bottom of the column is selected to maintain this pressure range.

Under these pressure conditions, the distillation temperature is then in the range from 50 to 200° C., preferably from 80 to 180° C., measured at the side offtakes.

To be able to operate the dividing wall column in a trouble-free manner, the abovementioned regulation mechanisms are usually employed in combination.

The sum of the number of theoretical plates in the enrichment section 2 and stripping section 4 in the inflow part is preferably from 80 to 110%, more preferably from 90 to 100%, of the sum of the number of theoretical plates in the enrichment section 3 and stripping section 5 in the offtake part and the region of thermal coupling 7 of the side offtakes.

The division of the liquid flowing down from the stripping section 3 of the offtake part of the column between the side offtake and the enrichment section 5 of the offtake part is set by means of a regulation device so that the quantity of liquid flowing into the enrichment section cannot drop below 30% of the normal value.

For example, the product stream in which the propylene glycols are present can be divided by means of the regulation principle described so that the low boilers LS comprising, for example, water and solvent, can be taken off via the top of the dividing wall column and be condensed in the condenser K. The intermediate boilers are taken off via the upper side offtake in the form of propylene glycol PG and via the lower side offtake in the form of dipropylene glycol DPG. The high boilers HS comprising the tripropylene glycol TPG can be obtained at the bottom of the column.

In the separation of multicomponent mixtures into low-boiling, intermediate-boiling and high-boiling fractions, there are usually specifications in respect of the maximum permissible proportion of low boilers and high boilers in the middle fraction. Here, individual components which are critical to the separation problem, referred to as key components, or else the sum of a plurality of key components are/is specified.

Adherence to the specification for the high boilers in the intermediate-boiling fraction is preferably regulated via the division ratio of the liquid at the upper end of the dividing wall 8. The division ratio is set so that the concentration of key components for the high-boiling fraction in the liquid at the upper end of the dividing wall amounts to from 10 to 80% by weight, preferably from 30 to 50% by weight, of the value which is to be achieved in the stream taken off at the side. The liquid division can then be set so that when the concentration of key components of the high-boiling fraction is higher, more liquid is introduced into the inflow part, and when the concentration of key components is lower, less liquid is introduced into the inflow part.

Accordingly, the specification for the low boilers LS in the intermediate-boiling fraction is regulated by means of the heating power. Here, the heating power in the vaporizer V is set so that the concentration of key components for the low-boiling fraction in the liquid at the lower end of the dividing wall 8 amounts to from 10 to 80% by weight, preferably from 30 to 50% by weight, of the value which is to be achieved in the product taken off at the side. Thus, the heating power is set so that when the concentration of key components of the low-boiling fraction is higher, the heating power is increased, and when the concentration of key components of the low-boiling fraction is lower, the heating power is reduced.

The concentration of low and high boilers in the intermediate-boiling fraction can be determined by customary analytical methods. For example, infrared spectroscopy can be used for detection, with the compounds present in the reaction mixture being identified by means of their characteristic absorptions. These measurements can be carried out in-line directly in the column. However, preference is given to using gas-chromatographic methods. In this case, sampling facilities are then provided at the upper and lower end of the dividing wall. Liquid or gaseous samples can then be taken off continuously or at intervals from the column and analyzed to determine their compositions. The appropriate regulation mechanisms can then be activated as a function of the composition.

An objective of the process of the present invention is to provide the intermediate boilers propylene glycol PG and dipropylene glycol DPG in a purity in each case of preferably greater than 95%, more preferably greater than 99%.

A mixture comprising the tripropylene glycol TPG is then taken from the bottom of the dividing wall column and passed to a distillation column which is thermally coupled with the dividing wall column.

According to the present invention, energy is introduced via the dividing wall column by means of the vaporizer V. Vapor and liquid exchange d and f occurs in the lower region of the dividing wall column and thus of the column which is thermally coupled therewith.

In the thermally coupled column, the tripropylene glycol TPG can be distilled off via the top of the column at a pressure of preferably from 5 to 500 mbar, more preferably from 10 to 200 mbar, and a temperature of preferably from 100 to 200° C., more preferably from 120 to 180° C. It is then condensed in the condenser K in which the stream of dipropylene glycol DPG can be used as coolant. The tripropylene glycol is preferably obtained in a purity of at least 95%.

Products having a boiling point higher than that of tripropylene glycol TPG which condense out are recirculated together with the bottoms from the thermally coupled column as liquid stream f to the dividing wall column. There, they can finally be taken off as high boilers HS in the bottoms from the column and passed, for example, to incineration. Examples of such bottom products are polypropylene glycols.

The thermally coupled column in which the tripropylene glycol is separated off can likewise be configured as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical plate.

The coupling of the continuous preparation of propylene oxide with the preparation of the propylene glycols, which is likewise carried out continuously, helps make the continuous process of the present invention extraordinarily advantageous for industrial use. For the purposes of the present invention, continuous means that the steps (i), (ii) and (iii) of the process of the present invention are carried out simultaneously.

A backward-integrated process starting from propylene is thus provided for the continuous preparation of propylene glycol, dipropylene glycol and tripropylene glycol. Since the purification by distillation of the propylene oxide and the distillation in three columns described in the prior art are dispensed with, a comparative saving in energy costs of about 30% can be achieved together with a reduced layout in terms of apparatus.

The process of the present invention will be outlined once more with the aid of the figure.

In zone A, hydrogen peroxide is reacted with propylene P to form propylene oxide. This gives, after work-up, crude propylene oxide PO(1) and the propylene glycols G as secondary yield.

The crude propylene oxide PO(1) is then passed to the zone C where it is reacted with water to give propylene glycols. In zone D the water is removed from these and can recirculated to the reaction with propylene oxide PO(1) to form propylene glycols.

The stream obtained from zone D is combined with the secondary yield of propylene glycols G and fed into the dividing wall column via the feed point Z. Propylene glycol PG and dipropylene glycol DPG are separated off in the dividing wall column and triproylene glycol TPG is separated off in the column which is thermally coupled therewith.

It is also possible to branch off a substream from the product stream PO(1) and process it in zone B to give pure propylene oxide PO(2) which can, for example, have a purity of more than 99.9%.

"Chemical grade" propylene can be used for the process of the present invention. Such propylene contains propane and has a volume ratio of propylene to propane of from about 97:3 to 95:5.

The hydrogen peroxide used for the reaction is preferably in the form of an aqueous hydrogen peroxide solution. It can be prepared, for example, by means of the anthraquinone process as described in "Ullmann's Encyclopedia of Industrial Chemistry", 5th Edition, Volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulftric acid then leads via peroxomonosulfiric acid to hydrogen peroxide and sulfuric acid, which is thus recovered.

It is of course also possible to prepare hydrogen peroxide from the elements.

As solvents for the preparation of propylene oxide, it is preferably possible to use all solvents which completely or at least partly dissolve the starting materials used in the oxirane synthesis. Examples of solvents which can be used are water; alcohols, preferably lower alcohols, more preferably alcohols having less than 6 carbon atoms, for example, methanol, ethanol, propanols, butanols, pentanols, diols or polyols, preferably those having less than 6 carbon atoms; ethers such as diethyl ether, tetrahydrofuran, dioxane, 1,2-diethoxyethane, 2-methoxyethanol; esters such as methyl acetate or butyrolactone; amides such as dimethylformamide, dimethylacetamide, N-methylpyrrolidone; ketones such as acetone; nitriles such as acetonitrile; sulfoxides such as dimethyl sulfoxide; aliphatic, cycloaliphatic and aromatic hydrocarbons, or mixtures of two or more of the abovementioned compounds.

Preference is given to using alcohols. The use of methanol as solvent is particularly preferred.

As catalysts for the preparation of propylene oxide, preference is given to using those which comprise a porous oxidic material, e.g. a zeolite. The catalysts used preferably comprise a titanium-, germanium-, tellurium-, vanadium-, chromium-, niobium- or zirconium-containing zeolite.

Specific mention may be made of titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures comprising two or more of the abovementioned structures. Furthermore, titanium-containing zeolites having the ITQ-4, SSZ-24, TTM-1, UTD-1, CIT-1 or CIT-5 structure are also conceivable for use in the process of the present invention. Further titanium-containing zeolites which may be mentioned are those of the ZSM-48 or ZSM-12 structure.

Particular preference is given to using Ti-zeolites having an MFI or MEL structure or an MFI/MEL mixed structure. Very particular preference is given to the specific titanium-containing zeolite catalysts which are generally referred to as "TS-1", "TS-2", "TS-3" and also Ti zeolites having a framework structure isomorphous with R-zeolite.

The use of a heterogeneous catalyst comprising the titanium-containing silicalite TS-1 is very advantageous.

In general, the reaction temperature for the preparation of the propylene oxide in steps ($\alpha$) and ($\gamma$) is in the range from 0 to 120° C., preferably in the range from 10 to 100° C. and more preferably in the range from 20 to 90° C. The pressures which prevail range from 1 to 100 bar, preferably from 1 to 40 bar, more preferably from 1 to 30 bar. Preference is given to working at pressures under which no gas phase is present.

The concentration of propylene and hydrogen peroxide in the feed stream is generally selected so that the molar ratio is preferably in the range from 0.7 to 20, more preferably in the range from 0.8 to 5.0, particularly preferably in the range from 0.9 to 2.0 and in particular in the range from 1.0 to 1.6.

In the preparation of propylene oxide, the residence times in the reactor or reactors depend essentially on the desired conversions. In general, they are less than hours, preferably less than 3 hours, more preferably less than 1 hour and particularly preferably about half an hour.

To reduce the hydroperoxy alcohols present in the product mixture from the preparation of propylene oxide, it is possible to employ the methods described in DE 10105 527.7.

For example, phosphorus(III) compounds such as phosphorus trichloride, phosphines (e.g. triphenylphosphine, tributylphosphine), phosphorous acid or its salts or sodium hyphophosphite can be used.

Reduction using sulfur(II) compounds such as hydrogen sulfide or salts thereof, sodium polysulfides, dimethyl sulfide, tetrahydrothiophene, bis(hydroxyethyl) sulfide or sodium thiosulfate or using sulfur(IV) compounds such as sulfurous acid and its salts, sodium bisulfite or thiourea-S-oxide is also possible.

Further reducing agents are nitrites, for example, sodium nitrite or isoamyl nitrite $\alpha$-Hydroxycarbonyl compounds such as hydroxyacetone, dihydroyactone, 2-hydroxycylopentanone (glutaroin), 2-hydroxycyclohexanone (adipoin), glucose and other reducing sugars are also suitable. Ene diols such as ascorbic acid or compounds which contain a boron-hydrogen bond, for example, sodium borohydride or sodium cyanoborohydride, can likewise be used.

However, the product mixtures comprising $\alpha$-hydroperoxy alcohols are preferably reduced by means of catalytic hydrogenation using hydrogen, which can be carried out in a homogeneous or heterogeneous phase. The hydrogenation catalyst comprises at least one active metal from transition groups VIIb, VIII, 1a and 1b of the Periodic Table of the Elements, either individually or as a mixture of two or more thereof. For example, palladium (Pd), platinum (Pt), rhodium (Rh), ruthenium (Ru), iridium (Ir), osmium (Os), iron (Fe), cobalt (CO), nickel (Ni) and copper (Cu), preferably Pd, Pt, Rh, Ru and Ir, particularly preferably Pd, can be used. These catalysts can be used either in powder form or as bodies made of active metal. Preference is given to using foils, wires, meshes, granules and crystallized powders produced from at least one active metal or a mixture of two or more thereof. It is also possible to use active metal oxides, for example, as suspensions of at least one active metal or a mixture of two or more thereof.

The present invention further provides an apparatus for carrying out a continuous process for preparing propylene glycols comprising at least one reactor for preparing propylene oxide, at least one reactor for reacting the propylene oxide with water to form propylene glycols, at least one dewatering apparatus for dewatering the water-containing propylene glycols and at least one dividing wall column having two side offtakes for separating off propylene glycol and dipropylene glycol and a column which is thermally coupled therewith for separating off the tripropylene glycol.

In a particularly preferred embodiment of the apparatus of the present invention, the at least one reactor consists of an isothermal fixed-bed reactor for carrying out the step ($\alpha$), an adiabatic fixed-bed reactor for carrying out the step ($\gamma$) and a separation apparatus for carrying out the step ($\beta$).

The reactions of propylene with hydrogen peroxide in the steps ($\alpha$) and ($\gamma$) are carried out in the isothermal reactor and the adiabatic reactor, respectively. Unreacted hydrogen peroxide from step ($\alpha$) is separated off in step ($\beta$) in the separation apparatus and is reacted once again with propylene in step ($\gamma$).

LIST OF REFERENCE NUMERALS FOR THE FIGURE

1 Combined region of the inflow and offtake part of the dividing wall column
2 Enrichment section of the inflow part
3 Stripping section of the offtake part
4 Stripping section of the inflow part
5 Enrichment section of the offtake part
6 Combined region of the inflow and offtake part
7 Region of thermal coupling
8 Dividing wall
P Propylene
A Zone in which propylene oxide is prepared
PO(1) Crude propylene oxide
B Work-up zone for propylene oxide
PO(2) Purified propylene oxide
G Propylene glycols as secondary yield
C Zone in which propylene oxide is reacted with water
D Dewatering zone for the propylene glycols
Z Feed point
LS Low boilers
PG Propylene glycol
DPG Dipropylene glycol
TPG Triproylene glycol
HS High boilers
K Condenser
V Vaporizer
d Vapor
f Liquid Horizontal and diagonal or indicated diagonal lines in the columns symbolize packing made up of random packing elements or ordered packing which may be present in the column.

The invention claimed is:

1. An apparatus comprising:
a first reactor,
a first distillation column,
a second reactor,
a dewatering apparatus,
a dividing wall column having two side offtakes, and
a third distillation column thermally coupled to the dividing wall column;
wherein the first reactor is connected to the first distillation column by a first connection such that a content of the first reactor can be transferred to the first distillation column via the first connection,
wherein the first distillation column is connected to the second reactor by a second connection such that a top fraction of the first distillation can be transferred to the second reactor via the second connection,
wherein the first distillation column is connected to the dividing wall column by a third connection such that a bottoms fraction of the first distillation column can be transferred to the dividing wall column via the third connection,
wherein the second reactor is connected to the dewatering apparatus by a fourth connection such that a content of the second reactor can be transferred to the dewatering apparatus via the fourth connection,
wherein the dewatering apparatus is connected to the dividing wall column by a fifth connection such that a content of the dewatering apparatus, minus any water removed by the dewatering apparatus, can be transferred to the dividing wall column via the fifth connection,
wherein the third connection and the fifth connection are arranged such that the bottoms fraction of the first distillation column and the content of the dewatering apparatus, minus any water removed by the dewatering apparatus, can be combined prior to being transferred to the dividing wall column,
wherein the dividing wall column is connected to the third distillation column via a sixth connection such that a bottoms fraction of the dividing wall column can be transferred to the third distillation column via the sixth connection, and
wherein the sixth connection at the dividing wall column side of the connection is not connected to either of the two side offtakes.

2. The apparatus of claim 1,
wherein
the first reactor is configured to react propylene with hydrogen peroxide to form a crude reaction mixture,
the first distillation column is configured to separate the crude reaction mixture comprising propylene oxide, monopropylene glycol, dipropylene glycol, and tripropylene glycol into a bottoms fraction and a top fraction, the bottoms fraction comprising the monopropylene glycol, the dipropylene glycol, and the tripropylene glycol, and the top fraction comprising the propylene oxide,
the second reactor is configured to react propylene oxide with water to give a reacted mixture comprising monopropylene glycol, dipropylene glycol, tripropylene glycol and water,
the dewatering apparatus is configured to remove water from the reacted mixture to give a dewatered reaction mixture,
the dividing wall column having two side offtakes is configured to separate, from the dewatered reaction mixture, the monopropylene glycol via an upper side offtake of the two side offtakes and the dipropylene glycol via a lower side offtake of the two side offtakes, and the third distillation column thermally coupled to the dividing wall column is configured to separate the tripropylene glycol from the dewatered reaction mixture.

3. The apparatus of claim 1, wherein the first reactor further comprises a first reactor first input.

4. The apparatus of claim 3, wherein the first reactor first input is configured to deliver hydrogen peroxide to the first reactor.

5. The apparatus of claim 1, wherein the first reactor further comprises a first reactor second input.

6. The apparatus of claim 5, wherein the first reactor second input is configured to deliver propylene to the first reactor.

7. The apparatus of claim 1, wherein the first reactor further comprises a first reactor first input and a first reactor second input.

8. The apparatus of claim 7, wherein first reactor first input is configured to deliver hydrogen peroxide to the first reactor, and wherein the first reactor second input is configured to deliver propylene to the first reactor.

9. The apparatus of claim 1, wherein the second reactor further comprises a second reactor first input.

10. The apparatus of claim 9, wherein the second reactor first input is configured to deliver water to the second reactor.

11. The apparatus of claim 10, further comprising a seventh connection, wherein the dewatering apparatus is connected to the second reactor via the seventh connection such that water, removed by the dewatering apparatus, can be transferred to the second reactor via the seventh connection, and, wherein the second reactor first input and the seventh connection are arranged such that any water removed by the dewatering apparatus can be combined with water from the second reactor first input prior to being transferred to the second reactor.

12. The apparatus of claim 11, further comprising a first condenser, wherein the first condenser is connected to the dividing wall column by an eighth connection, such that low boilers can be transferred from the dividing wall column to the first condenser via the eighth connection, and wherein the eighth connection at the dividing wall column side of the connection is not connected to either of the two side offtakes.

13. The apparatus of claim 12, further comprising a second condenser, wherein the second condenser is connected to the third distillation column by a ninth connection.

14. The apparatus of claim 13, wherein, the two side offtakes comprise an upper side offtake and a lower side offtake, wherein the second condenser is connected to the upper side offtake by a tenth connection, and wherein the tenth connection is configured such that monopropylene glycol separated via the upper side offtake of the dividing wall column can be used as coolant in the second condenser.

* * * * *

UNITED STATES PATENT AND TRADEMARK OFFICE
CERTIFICATE OF CORRECTION

| | | |
|---|---|---|
| PATENT NO. | : 7,658,893 B2 | Page 1 of 1 |
| APPLICATION NO. | : 11/441153 | |
| DATED | : February 9, 2010 | |
| INVENTOR(S) | : Bassler et al. | |

It is certified that error appears in the above-identified patent and that said Letters Patent is hereby corrected as shown below:

On the title page, Item (30), the Foreign Application Priority Data has been omitted. Item (30) should read:

-- (30)     Foreign Application Priority Data

July 23, 2002   (DE).............................................. 102 33 385 --

Signed and Sealed this

Twentieth Day of April, 2010

David J. Kappos
*Director of the United States Patent and Trademark Office*